United States Patent
Liang et al.

(10) Patent No.: US 9,950,997 B2
(45) Date of Patent: Apr. 24, 2018

(54) METHOD FOR PREPARING HIGH-PURITY SULFONAMIDE COMPOUND, AND INTERMEDIATE OF SULFONAMIDE COMPOUND

(71) Applicant: ORIENTAL (LUZHOU) AGROCHEMICALS. CO., LTD., Sichuan (CN)

(72) Inventors: Xiaomin Liang, Hangzhou (CN); Hao Jiang, hangzhou (CN); Haige Teng, hangzhou (CN); Jinzhi Yang, hangzhou (CN); Junjin Zhou, hangzhou (CN); Jinlong Zhang, hangzhou (CN); Bangchi Chen, hangzhou (CN)

(*) Notice: Subject to any disclaimer, the term of this patent is extended or adjusted under 35 U.S.C. 154(b) by 0 days.

(21) Appl. No.: 15/700,136

(22) Filed: Sep. 10, 2017

(65) Prior Publication Data
US 2017/0369429 A1    Dec. 28, 2017

Related U.S. Application Data

(63) Continuation of application No. PCT/CN2015/073945, filed on Mar. 10, 2015.

(51) Int. Cl.
| | |
|---|---|
| C07C 303/40 | (2006.01) |
| C07C 311/21 | (2006.01) |
| C07D 487/04 | (2006.01) |
| C07D 239/50 | (2006.01) |
| C07D 249/16 | (2006.01) |
| A01N 43/90 | (2006.01) |
| B01J 31/02 | (2006.01) |
| C07C 311/51 | (2006.01) |
| C07C 311/53 | (2006.01) |
| C07C 303/44 | (2006.01) |

(52) U.S. Cl.
CPC ............ C07C 303/40 (2013.01); A01N 43/90 (2013.01); B01J 31/0224 (2013.01); C07C 303/44 (2013.01); C07C 311/21 (2013.01); C07C 311/51 (2013.01); C07C 311/53 (2013.01); C07D 239/50 (2013.01); C07D 249/16 (2013.01); C07D 487/04 (2013.01); C07C 2527/24 (2013.01)

(58) Field of Classification Search
None
See application file for complete search history.

(56) References Cited

U.S. PATENT DOCUMENTS

| | | | |
|---|---|---|---|
| 4,818,275 A * | 4/1989 | Theodoridis | A01N 43/653 504/273 |
| 4,910,306 A | 3/1990 | McKendry | |
| 5,010,195 A * | 4/1991 | Van Heertum | A01N 43/90 544/263 |
| 5,163,995 A * | 11/1992 | Van Heertum | A01N 43/90 504/241 |
| 5,858,924 A * | 1/1999 | Johnson | A01N 43/90 504/241 |
| 5,973,148 A | 10/1999 | Ringer et al. | |
| 2002/0111361 A1* | 8/2002 | Johnson | A01N 43/90 514/259.31 |
| 2004/0049041 A1* | 3/2004 | Ikemoto | C07C 303/40 544/383 |
| 2005/0215570 A1* | 9/2005 | Hamilton | C07D 471/04 514/259.31 |
| 2012/0149699 A1* | 6/2012 | Macielag | C07D 471/04 514/233.2 |

FOREIGN PATENT DOCUMENTS

| | | | |
|---|---|---|---|
| CN | 104447756 | * | 3/2015 |
| CN | 104447756 A | | 3/2015 |
| EP | 0142152 | * | 5/1985 |
| EP | 0142152 A2 | | 5/1985 |
| WO | 8703782 A1 | | 7/1987 |
| WO | 9813367 A1 | | 4/1998 |
| WO | WO 98/13367 | * | 4/1998 |
| WO | 9837065 A1 | | 8/1998 |
| WO | 0236595 A2 | | 5/2002 |
| WO | 2005097793 A1 | | 10/2005 |

OTHER PUBLICATIONS

Ebrahimi ("N-Acyl-N-(4-chlorophenyl)-4-nitrobenzene-sulfonamides: highly selective and efficient reagents for acylation of amines in water" Zeitschrift für Naturforschung. B, A journal of chemical sciences, vol. 71, issue 2, p. 95-104, 2016).*
Kondo ("Studies on Development of Sufficiently Chemoselective N-Acylation Reagents: N-Acyl-N-(2,3,4,5,6-pentafluorophenyl)methanesulfonamides" Tetrahedron, 56, 2000, p. 5843-5856).*
International search report for PCT/CN2015/073945, dated Feb. 19, 2016.*

* cited by examiner

Primary Examiner — Jafar Parsa
Assistant Examiner — Amy C Bonaparte
(74) Attorney, Agent, or Firm — Wayne & Ken, LLC; Tony Hom

(57) ABSTRACT

The present invention discloses a method for preparing a high-purity sulfonamide compound and an intermediate of the sulfonamide compound. The method comprises the following steps: a, taking a crude product of a sulfonamide compound (I) as an initial raw material, and enabling the raw material to react with a compound of a formula (II) in presence of alkali and a catalyst so as to synthesize an intermediate of a formula (III); and b, enabling the compound represented by the formula (III) to react with alkali or acid, thereby obtaining the high-purity sulfonamide compound (I).

7 Claims, No Drawings

METHOD FOR PREPARING HIGH-PURITY SULFONAMIDE COMPOUND, AND INTERMEDIATE OF SULFONAMIDE COMPOUND

FIELD OF THE INVENTION

The present invention relates to synthesis of organosulfur compounds, and more specifically, to a method for preparing a high-purity sulfonamide compound and an intermediate of the sulfonamide compound.

BACKGROUND OF THE INVENTION

Sulfonamide compounds (I) are a class of very important organosulfur compounds and are widely used in pesticide. For example, diclosulam (N-(2,6-dichlorophenyl)-5-ethoxy-7-fluoro-1,2,4-triazolo[1,5-c]pyrimidine-2-sulfamide) developed by Dow Agroscience Company is a triazolopyrimidine sulfamide high-potent herbicide (U.S. Pat. No. 5,163,995). Diclosulam is an acetolactate synthetase (ALS) inhibitor and can be rapidly absorbed by roots and stem leaves of weeds to achieve effects. Diclosulam is applied to pre-emergence treatment of planting soil in fields of crops such as soybeans and peanuts for controlling broadleaf weeds and is used for post-emergence control of broadleaf weeds in winter wheat fields.

Diclosulam can be prepared by condensing 2,6-dichloroaniline and triazolopyrimidine sulfonyl chloride. Since 2,6-dichloroaniline has extremely high steric hindrance, the condensation reaction between the 2,6-dichloroaniline and the triazolopyrimidine sulfonyl chloride is slow and the yield is low, resulting in low purity of a product. Although the reaction is improved in U.S. Pat. No. 5,973,148 and the reaction yield is increased, 3% of triazolopyrimidine sulfonic acid is still contained in the product. Due to its chemical and physical properties of diclosulam cannot be effectively refined through base-dissolving acid-crystallizing method. In addition, since diclosulam has low solubility in conventional solvents, it is difficult to be obtain high-purity diclosulam through a recrystallization method while taking the yield into account at the same time.

For other novel high-potent herbicides such as sulfentrazone (N-(2,4-dichloro-5-[4-difluoromethyl-4,5-dihydro-3-methyl-5-oxo-1H-1,2,4-triazole-1-yl]phenyl)methane sulfonamide, WO 8703782), cloransulam methyl (3-chloro-2-[(5-ethoxy-7-fluoro-1,2,4-triazolo[1,5-c]pyrimidine-2-yl) sulfonamide]methyl benzoate U.S. Pat. No. 5,163,995), florasulam (N-(2,6-difluorophenyl)-5-ethoxy-8-fluoro-1,2,4-triazolo[1,5-c]pyrimidine-2-sulfamide, U.S. Pat. No. 5,163,995), penoxsulam (2-(2,2-difluoroethoxy)-N-(5,8-dimethoxy-1,2,4-triazolo[1,5-c]pyrimidine-2-yl)-6-trifluoromethyl benzenesulfonamide, U.S. Pat. No. 5,858,924), flumetsulam (N-2,6-difluorophenyl)-5-methyl-1,2,4-triazolo[1,5-a]pyrimidine-2-sulfamide, U.S. Pat. No. 4,910,306), pyroxsulam (N-(5,7-dimethoxy-1,2,4-triazolo[1,5-a]pyrimidine-2-yl)-2-methoxy-4-trifluoromethyl-3-pyridinesulfonamide, WO 2002036595), metosulam (N-(2,6-dichloro-3-methylphenyl)-5,7-dimethoxy-1,2,4-triazolo[1,5-a]pyrimidine-2-sulfamide, EP 0142152), etc., there exist similar technical problems due to similar chemical and physical properties.

SUMMARY OF THE INVENTION

A purpose of the present invention is to provide a method for preparing a high-purity sulfonamide compound and an intermediate of the sulfonamide compound in order to overcome the above technical shortcomings in the prior arts, so as to meet needs of scientific research and industrial production.

A method for preparing a high-purity sulfonamide compound comprises the following steps:

step a, reacting with a compound of a formula (II) under the action of a solvent, a base and a catalyst by taking a crude product of a sulfonamide compound (I) as an initial raw material, so as to synthesize a compound of a formula (III); and step b, enabling the compound represented by the formula (III) to react with a base or an acid in a solvent, thereby obtaining the high-purity sulfonamide compound (I).

A general formula of the reactions is as follows:

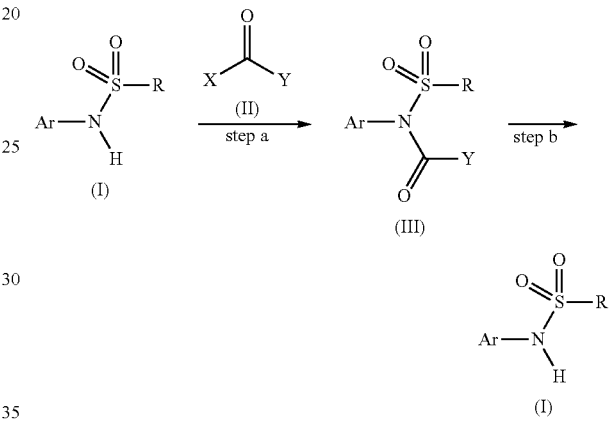

wherein R is methyl, or aryl or heteroaryl shown as follows:

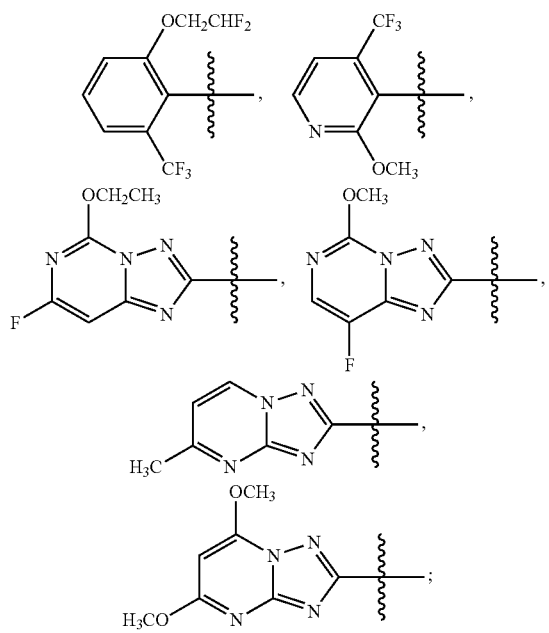

Ar is aryl or heteroaryl shown as follows:

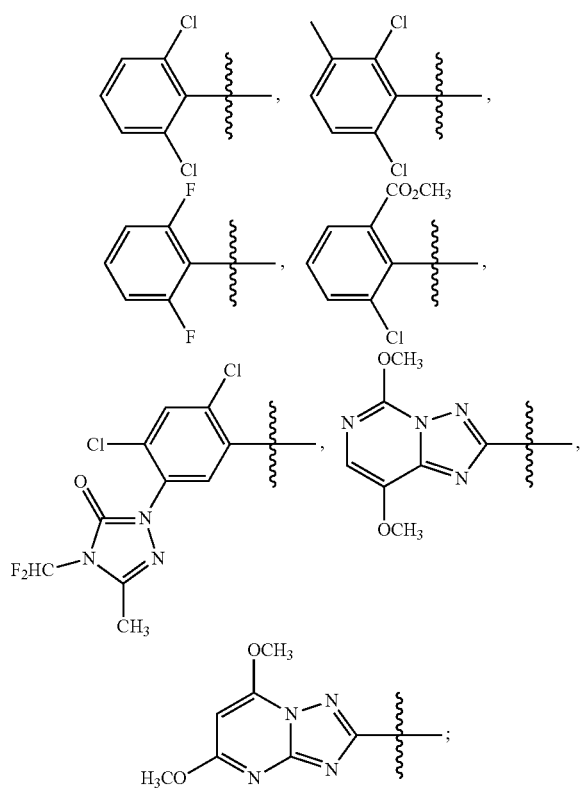

X is halogen or tert-butoxy carbonyloxy.

Y is C1-C6 alkyl, C6-C12 aryl or tert-butoxy.

X is preferably Cl or tert-butoxy carbonyloxy, and Y is preferably C1-C6 alkyl or tert-butoxy.

The molar ratio of the compound (II) to the crude product of the sulfonamide compound (I) is (0.8-2):1.

The base in the step a is organic base; the molar ratio of the organic base to the crude product of the sulfonamide compound (I) is (1-2):1; the catalyst is 4-dimethylaminopyridine; the weight percentage of the catalyst to the crude product of the sulfonamide compound (I) is 0.05-10%; the solvent is halohydrocarbons or ethers or nitriles; and the reaction temperature is −10° C.-80° C.

The organic base in the step a is preferably triethylamine, DBU or pyridine; a molar ratio of the organic base to the crude product of the sulfonamide compound (I) is preferably (1-1.3):1; the weight percentage of the catalyst to the crude product of the sulfonamide compound (I) is preferably 0.1-5%; the solvent is preferably dichloromethane or tetrahydrofuran or acetonitrile; and the reaction temperature is preferably 0° C.-40° C.

The base in the step b is hydroxide, carbonate or hydrocarbonate of alkali metals and alkaline-earth metals, the molar ratio of the alkali to the compound (III) is (0.5-1.5):1, the solvent is methanol, ethanol, isopropanol, acetonitrile, acetone, DMF or DMSO, and the reaction temperature is 0° C.-80° C.; or the acid in the step b is an inorganic acid or an organic acid, the molar ratio of the acid to the compound (III) is (0.5-1.5):1, the solvent is methanol, ethanol, isopropanol, acetonitrile, acetone, DMF or DMSO, and the reaction temperature is 0° C.-80° C.

The base in the step b is preferably sodium carbonate, potassium carbonate, sodium bicarbonate or potassium bicarbonate, the molar ratio of the base to the compound (III) is preferably (0.75-1.25):1, the solvent is preferably ethanol, and the reaction temperature is preferably 10° C.-60° C.; or the acid in the step b is preferably hydrochloric acid, sulfuric acid or trifluoroacetic acid, the molar ratio of the acid to the compound (III) is preferably (0.75-1.25):1, the solvent is preferably ethanol, and the reaction temperature is preferably 10° C.-60° C.

The present invention provides a sulfonamide compound. The structure of the compound is shown in a formula (III) as follows:

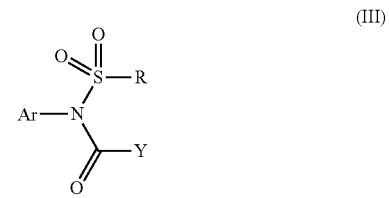

wherein R is methyl, or aryl or heteroaryl shown as follows:

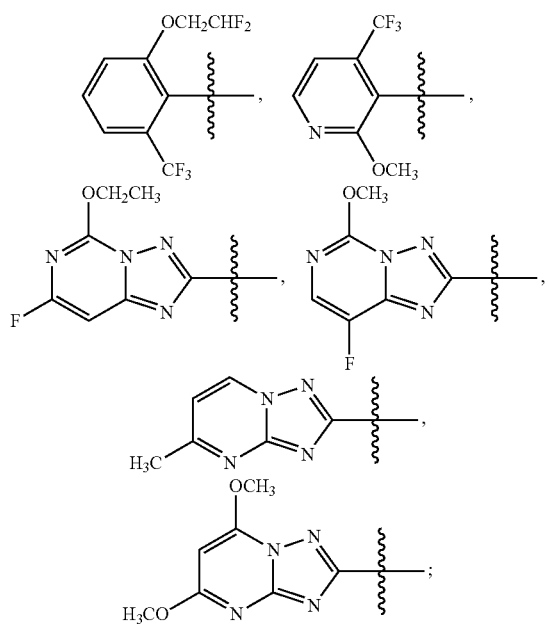

Ar is aryl or heteroaryl shown as follows:

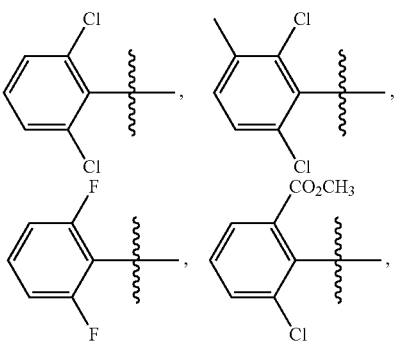

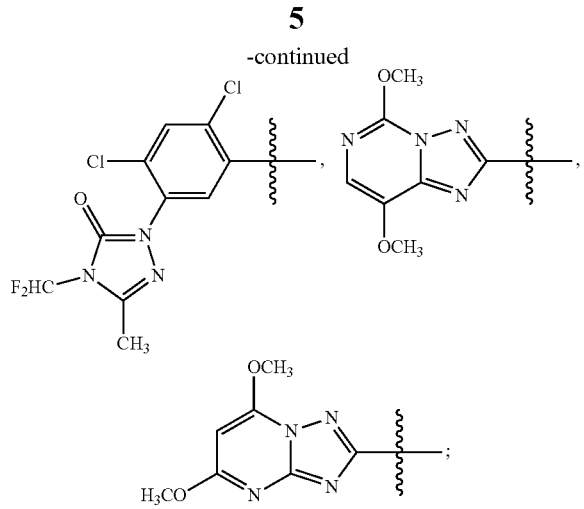

Y is C1-C6 alkyl, C6-C12 aryl or tert-butoxy.

Y is preferably C1-C6 alkyl or tert-butoxy.

Compared with the prior arts, the present invention has benefits as follows:

The present invention is characterized by transformation of difficult-to-purify crude sulfonamide compound (I) which has poor solubility in a conventional solvent into an intermediate (II) which is freely soluble in the conventional solvents, followed by purification, and simple hydrolysis to give high-purity sulfonamide compound (I). HPLC purity of the sulfonamide compound prepared by the present invention can reach 99.9% or higher.

The present invention uses cheap reagents, is simple operation, gives high yield, and high purity of the prepared product has great application values in scientific research and production of sulfonamide drugs.

DETAILED DESCRIPTION OF THE INVENTION

To understand technical contents of the present invention more clearly, the present invention is further described with reference to the following embodiments, but the present invention is not limited by the following embodiments.

Embodiment 1 Preparation of N-acetyl-N-(2,6-dichlorophenyl)-5-ethoxy-7-fluoro-1,2,4-triazolo[1,5-c]pyrimidine-2-sulfamide The preparation method comprises the following steps:
sequentially adding a crude product of N-(2,6-dichlorophenyl)-5-ethoxy-7-fluoro-1,2,4-triazolo[1,5-c]pyrimidine-2-sulfamide (HPLC purity is 95.8%) (10.0 g, 1.0 eq), DMAP (0.01 g), acetonitrile (100 mL) and triethylamine (3.0 g, 1.2 eq) into a 250 mL reaction flask at room temperature, and dropwise adding acetyl chloride (2.1 g, 1.1 eq); continuously reacting for 3 h after finishing dropwise adding, stopping the reaction when the raw materials are completely reacted as determined by HPLC, distilling to remove the acetonitrile and adding water, extracting for three times with dichloromethane, merging organic phases, washing with brine and drying with anhydrous magnesium sulfate, washing the white solid obtained by filtering and concentrating with ethanol, and drying to obtain 10.3 g of the white solid, the HPLC purity is 99.1%. $^1$H NMR (400 MHz, D6-DMSO) δ: 7.72 (m, 2H), 7.62 (m, 1H), 7.50 (s, 1H), 4.73 (m, 2H), 2.12(s, 3H), 1.48 (m, 3H).

Embodiment 2 Preparation of N-(2-bromoacetyl)-N-(2,6-dichlorophenyl)-5-ethoxy-7-fluoro-1,2,4-triazolo[1,5-c]pyrimidine-2-sulfamide The preparation method comprises the following steps:
sequentially adding a crude product of N-(2,6-dichlorophenyl)-5-ethoxy-7-fluoro-1,2,4-triazolo[1,5-c]pyrimidine-2-sulfamide (HPLC purity of 95.8%) (10.0 g, 1.0 eq), DMAP (0.01 g), THF (100 mL) and triethylamine (3.0 g, 1.2 eq) into a 250 mL reaction flask at room temperature, and dropwise adding bromoacetyl bromide (5.5 g, 1.1 eq); continuously reacting for 2 h after finishing dropwise adding, stopping the reaction when the raw materials are completely reacted as determined by HPLC, distilling to remove the THF and adding water, extracting for three times with dichloromethane, merging organic phases, washing with brine and then drying with anhydrous magnesium sulfate, washing the white solid obtained by filtering and concentrating with ethanol, and drying to obtain 12.3 g of the white solid, wherein the HPLC purity is 99.5%. $^1$H NMR (400 MHz, D6-DMSO) δ: 7.76 (m, 2H), 7.68 (m, 1H), 7.57 (s, 1H), 4.87 (s, 2H), 4.76 (m, 2H), 1.50 (m, 3H).

Embodiment 3 Preparation of N-(2-chloracetyl)-N-(2,6-dichlorophenyl)-5-ethoxy-7-fluoro-1,2,4-triazolo[1,5-c]pyrimidine-2-sulfamide The preparation method comprises the following steps:
sequentially adding a crude product of N-(2,6-dichlorophenyl)-5-ethoxy-7-fluoro-1,2,4-triazolo[1,5-c]pyrimidine-2-sulfamide (HPLC purity of 95.8%) (10.0 g, 1.0 eq), DMAP (0.01 g), THF (100 mL) and triethylamine (3.0 g, 1.2 eq) into a 250 mL reaction flask at room temperature, and dropwise adding chloroacetyl chloride (3.1 g, 1.1 eq); continuously reacting for 2 h after finishing dropwise adding, stopping the reaction when the raw materials are completely reacted as determined by HPLC, distilling to remove the THF and adding water, extracting for three times with dichloromethane, merging organic phases, washing with brine and then drying with anhydrous magnesium sulfate, washing the white solid obtained by filtering and concentrating with ethanol, and drying to obtain 11.4 g white solid, wherein the HPLC purity is 99.3%. $^1$H NMR (400 MHz, D6-DMSO) δ: 7.72 (m, 2H), 7.62 (m, 1H), 7.50 (s, 1H), 4.97 (s, 2H), 4.73 (m, 2H), 1.48 (m, 3H).

Embodiment 4 Preparation of N-(2,2-dichloroacetyl)-N-(2,6-dichlorophenyl)-5-ethoxy-7-fluoro-1,2,4-triazolo[1,5-c]pyrimidine-2-sulfamide The preparation method comprises the following steps:
sequentially adding a crude product of N-(2,6-dichlorophenyl)-5-ethoxy-7-fluoro-1,2,4-triazolo[1,5-c]pyrimidine-2-sulfamide (HPLC purity is 95.8%) (10.0 g, 1.0 eq), DMAP (0.01 g), THF (100 mL) and triethylamine (3.0 g, 1.2 eq) into a 250 mL reaction flask at room temperature, and dropwise adding dichloracetyl chloride (4.0 g, 1.1 eq); continuously reacting for 1 h after finishing dropwise adding, stopping the reaction when the raw materials are completely reacted as determined by HPLC, distilling to remove the THF and adding water, extracting for three times with dichloromethane, merging organic phases, washing with brine and then drying with anhydrous magnesium sulfate, washing the white solid obtained by filtering and concentrating with ethanol, and drying to obtain 11.6 g white solid, and the HPLC purity is 99.0%. $^1$H NMR (400 MHz, D6-DMSO) δ: 7.75 (m, 2H), 7.63 (m, 1H), 7.54 (s, 1H), 6.80 (s, 1H), 4.78 (m, 2H), 1.46 (m, 3H).

Embodiment 5 Preparation of N-benzoyl-N-(2,6-dichlorophenyl)-5-ethoxy-7-fluoro-1,2,4-triazolo[1,5-c]pyrimidine-2-sulfamide N-benzoyl-N-(2,6-dichlorophenyl)-5-ethoxy-7-fluoro-1,2,4-triazolo[1,5-c]pyrimidine-2-sulfamide is prepared by a method similar to that in embodiment 1, it is a white solid and the HPLC purity is 98.7%. $^1$H NMR (400 MHz, D6-DMSO) δ: 7.95-6.86 (m, 9H), 3.98 (m, 2H), 1.33 (m, 3H).

Embodiment 6 Preparation of N-(2-methoxyacetyl)-N-(2,6-dichlorophenyl)-5-ethoxy-7-fluoro-1,2,4-triazolo[1,5-c]pyrimidine-2-sulfamide N-(2-methoxyacetyl)-N-(2,6-dichlorophenyl)-5-ethoxy-7-fluoro-1,2,4-triazolo[1,5-c]pyrimidine-2-sulfamide is prepared by a method similar to that in embodiment 1, it is a white solid and the HPLC purity is 98.8%. $^1$H NMR (400 MHz, D6-DMSO) δ: 7.70-7.71 (m, 2H), 7.60-7.61 (m, H), 7.49 (s, H), 4.74 (q, 2H), 4.57 (s, 3H), 1.47 (t, 3H).

Embodiment 7 Preparation of 2-(2,2-difluoroethoxyl)-N-(2-chloracetyl)-N-(5,8-dimethoxy-1,2,4-triazolo[1,5-c]pyrimidine-2-yl)-6-trifluoromethyl benzenesulfonamide 2-(2,2-difluoroethoxyl)-N-(2-chloracetyl)-N-(5,8-dimethoxy-1,2,4-triazolo[1,5-c]pyrimidine-2-yl)-6-trifluoromethyl benzenesulfonamide is prepared by a method similar to that in embodiment 1, it is a white solid and the HPLC purity is 98.9%. NMR (400 MHz, D6-DMSO) δ: 7.72-7.96 (m, 4H), 6.75 (t, 1H), 4.77 (m, 2H), 4.35 (s, 2H), 4.20 (s, 3H), 4.04 (s, 3H).

Embodiment 8 Preparation of 2-(2,2-difluoroethoxyl)-N-acetyl-N-(5,8-dimethoxy-1,2,4-triazolo[1,5-c]pyrimidine-2-yl)-6-trifluoromethyl benzenesulfonamide 2-(2,2-difluoroethoxyl)-N-acetyl-N-(5,8-dimethoxy-1,2,4-triazolo[1,5-c]pyrimidine-2-yl)-6-trifluoromethyl benzenesulfonamide is prepared by a method similar to that in embodiment 1, it is a white solid, and the HPLC purity is 98.7%. $^1$H NMR (400 MHz, D6-DMSO) δ: 7.70-7.92 (m, 4H), 6.76 (t, 1H), 4.78 (m, 2H), 4.20 (s, 3H), 4.02 (s, 3H), 1.95 (s, 3H).

Embodiment 9 Preparation of 2-(2,2-difluoroethoxyl)-N-benzoyl-N-(5,8-dimethoxy-1,2,4-triazolo[1,5-c]pyrimidine-2-yl)-6-trifluoromethyl benzenesulfonamide 2-(2,2-difluoroethoxyl)-N-benzoyl-N-(5,8-dimethoxy-1,2,4-triazolo[1,5-c]pyrimidine-2-yl)-6-trifluoromethyl benzenesulfonamide is prepared by a method similar to that in embodiment 1, it is a white solid, and the HPLC purity is 99.0%. NMR (400 MHz, D6-DMSO) δ: 7.31-7.96 (m, 9H), 6.35 (t, 1H), 4.64 (m, 2H), 4.13 (s, 3H), 3.94 (s, 3H).

Embodiment 10 Preparation of 2-(2,2-difluoroethoxyl)-N-(2-methoxyacetyl)-N-(5,8-dimethoxy-1,2,4-triazolo[1,5-c]pyrimidine-2-yl)-6-trifluoromethyl benzenesulfonamide 2-(2,2-difluoroethoxyl)-N-(2-methoxyacetyl)-N-(5,8-dimethoxy-1,2,4-triazolo[1,5-c]pyrimidine-2-yl)-6-trifluoromethyl benzenesulfonamide is prepared by a method similar to that in embodiment 1, it is a white solid, and the HPLC purity is 98.8%. NMR (400 MHz, D6-DMSO) δ: 7.70-7.92 (m, 4H), 6.70 (t, 1H), 4.74 (m, 2H), 4.17 (s, 3H), 3.99 (s, 3H), 3.82 (s, 2H), 3.13 (s, 3H).

Embodiment 11 Preparation of N-(2-methoxyacetyl)-3-chloro-2-[(5-ethoxy-7-fluoro-1,2,4-triazolo[1,5-c]pyrimidine-2-yl)sulfonamide]methyl benzoate N-(2-methoxyacetyl)-3-chloro-2-[(5-ethoxy-7-fluoro-1,2,4-triazolo[1,5-c]pyrimidine-2-yl)sulfonamide]methyl benzoate is prepared by a method similar to that in embodiment 1, and the HPLC purity is 95.9%. $^1$H NMR (400 MHz, D6-DMSO) δ: 7.99 (t, 2H), 7.73 (t, 1H), 7.46 (s, 1H), 4.74 (q, 2H), 3.69 (s, 1H), 3.67 (s, 3H), 3.28 (s, 3H), 1.98 (s, 1H), 1.50 (t, 3H).

Embodiment 12 Preparation of N-benzoyl-3-chloro-2-[(5-ethoxy-7-fluoro-1,2,4-triazolo[1,5-c]pyrimidine-2-yl)sulfonamide]methyl benzoate N-benzoyl-3-chloro-2-[(5-ethoxy-7-fluoro-1,2,4-triazolo[1,5-c]pyrimidine-2-yl)sulfonamide]methyl benzoate is prepared by a method similar to that in embodiment 1, and the HPLC purity is 99.1%. $^1$H NMR (400 MHz, D6-DMSO) δ: 7.87-7.89 (m, 2H), 7.60-7.62 (m, 1H), 7.52-7.53 (m, 2H), 7.40-7.43 (m, 2H), 7.28-7.31 (m, 2H), 4.74 (q, 2H), 3.78 (s, 3H), 1.51 (t, 3H).

Embodiment 13 Preparation of N-acetyl-3-chloro-2-[(5-ethoxy-7-fluoro-1,2,4-triazolo[1,5-c]pyrimidine-2-yl)sulfonamide]methyl benzoate N-acetyl-3-chloro-2-[(5-ethoxy-7-fluoro-1,2,4-triazolo[1,5-c]pyrimidine-2-yl)sulfonamide]methyl benzoate is prepared by a method similar to that in embodiment 1, and the HPLC purity is 99.2%. $^1$H NMR (400 MHz, D6-DMSO) δ: 7.94-7.98 (m, 2H), 7.71 (t, 1H), 7.45 (s, 1H), 4.73 (t, 2H), 3.66 (s, 3H), 1.49 (t, 3H).

Embodiment 14 Preparation of N-(2-chloracetyl)-3-chloro-2-[(5-ethoxy-7-fluoro-1,2,4-triazolo[1,5-c]pyrimidine-2-yl)sulfonamide]methyl benzoate N-(2-chloracetyl)-3-chloro-2-[(5-ethoxy-7-fluoro-1,2,4-triazolo[1,5-c]pyrimidine-2-yl)sulfonamide]methyl benzoate is prepared by a method similar to that in embodiment 1, and the HPLC purity is 98.2%. $^1$H NMR (400 MHz, D6-DMSO) δ: 7.97-8.02 (m, 2H), 7.76 (t, 1H), 7.46 (s, 1H), 4.73 (q, 2H), 3.66 (s, 3H), 1.50 (t, 3H).

Embodiment 15 Preparation of N-(2,2-dichloroacetyl)-3-chloro-2-[(5-ethoxy-7-fluoro-1,2,4-triazolo[1,5-c]pyrimidine-2-yl)sulfonamide]methyl benzoate N-(2,2-dichloroacetyl)-3-chloro-2-[(5-ethoxy-7-fluoro-1,2,4-triazolo[1,5-c]pyrimidine-2-yl)sulfonamide]methyl benzoate is prepared by a method similar to that in embodiment 1, and the HPLC purity is 97.1%. $^1$H NMR (400 MHz, D6-DMSO) δ: 8.00-8.05 (m, 2H), 7.78 (t, 1H), 7.41 (s, 1H), 4.73 (q, 2H), 3.67 (s, 3H), 1.51 (t, 3H).

Embodiment 16 Preparation of N-(2-methoxyacetyl)-N-[2,4-dichloro-5-(4-difluromethyl-4,5-dihydro-3-methyl-5-oxo-1H-1,2,4-triazol-1-yl)phenyl]methane sulfonamide N-(2-methoxyacetyl)-N-[2,4-dichloro-5-(4-difluromethyl-4,5-dihydro-3-methyl-5-oxo-1H-1,2,4-triazol-1-yl)phenyl]methane sulfonamide is prepared by a method similar to that in embodiment 1, and the HPLC purity is 95.9%. $^1$H NMR (400 MHz, D6-DMSO) δ: 8.19 (s, 1H), 8.10 (s, 1H), 7.46-7.65 (m, 1H), 3.96-3.98 (m, 1H), 3.80-3.83 (m, 1H), 3.62 (s, 3H), 3.26 (s, 3H), 2.42 (s, 3H).

Embodiment 17 Preparation of N-benzoyl-N-[2,4-dichloro-5-(4-difluromethyl-4,5-dihydro-3-methyl-5-oxo-1H-1,2,4-triazol-1-yl)phenyl]methane sulfonamide N-benzoyl-N-[2,4-dichloro-5-(4-difluromethyl-4,5-dihydro-3-methyl-5-oxo-1H-1,2,4-triazol-1-yl)phenyl]methane sulfonamide is prepared by a method similar to that in embodiment 1, and the HPLC purity is 99.8%. $^1$H NMR (400 MHz, D6-DMSO) δ: 8.22 (s, 1H), 7.97 (s, 1H), 7.54 (s, 2H), 7.48 (t, 2H), 7.34 (t, 2H), 7.31 (t, 2H), 3.70 (s, 3H), 2.40 (s, 3H).

Embodiment 18 Preparation of N-acetyl-N-[2,4-dichloro-5-(4-difluromethyl-4,5-dihydro-3-methyl-5-oxo-1H-1,2,4-triazol-1-yl)phenyl]methane sulfonamide N-acetyl-N-[2,4-dichloro-5-(4-difluromethyl-4,5-dihydro-3-methyl-5-oxo-1H-1,2,4-triazol-1-yl)phenyl]methane sulfonamide is prepared by a method similar to that in embodiment 1, and the HPLC purity is 99.8%. $^1$H NMR (400 MHz, D6-DMSO) δ: 8.20 (s, 1H), 8.08 (s, 1H), 7.46-7.64 (m, 1H), 3.60 (s, 3H), 2.42 (s, 3H), 2.00 (s, 3H).

Embodiment 19 Preparation of N-(2-chloracetyl)-N-[2,4-dichloro-5-(4-difluromethyl-4,5-dihydro-3-methyl-5-oxo-1H-1,2,4-triazol-1-yl)phenyl]methane sulfonamide N-(2-chloracetyl)-N-[2,4-dichloro-5-(4-difluromethyl-4,5-dihydro-3-methyl-5-oxo-1H-1,2,4-triazol-1-yl)phenyl]methane sulfonamide is prepared by a method similar to that in embodiment 1, and the HPLC purity is 95.8%. $^1$H NMR (400 MHz, D6-DMSO) δ: 8.19 (s, 1H), 8.10 (s, 1H), 7.48-7.65 (m, 1H), 4.27 (s, 2H), 3.64 (s, 3H), 2.42 (s, 3H).

Embodiment 20 Preparation of N-(2,2-dichloroacetyl)-N-[2,4-dichloro-5-(4-difluromethyl-4,5-dihydro-3-methyl-5-oxo-1H-1,2,4-triazol-1-yl)phenyl]methane sulfonamide N-(2,2-dichloroacetyl)-N-[2,4-dichloro-5-(4-difluromethyl-4,5-dihydro-3-methyl-5-oxo-1H-1,2,4-triazol-1-yl)phenyl]methane sulfonamide is prepared by a method similar to that in embodiment 1, and the HPLC purity is 95.8%. $^1$H NMR (400 MHz, D6-DMSO) δ: 8.19 (s, 1H), 8.17 (s, 1H), 7.65 (s, 1H), 7.46-7.66 (m, 1H), 6.65 (s, 1H), 3.70 (s, 3H), 2.42 (s, 3H).

Embodiment 21 Preparation of N-(2-methoxyacetyl)-N-(2,6-difluorophenyl)-5-ethoxy-8-fluoro-1,2,4-triazolo[1,5-c]pyrimidine-2-sulfamide N-(2-methoxyacetyl)-N-(2,6-difluorophenyl)-5-ethoxy-8-fluoro-1,2,4-triazolo[1,5-c]pyrimidine-2-sulfamide is prepared by a method similar to that in embodiment 1, and the HPLC purity is 98.6%. $^1$H NMR (400 MHz, D6-DMSO) δ: 8.41 (d, 1H), 7.71-7.74 (m, 1H), 7.41 (t, 2H), 4.35 (s, 2H), 4.26 (s, 3H), 3.25 (s, 3H).

Embodiment 22 Preparation of N-benzoyl-N-(2,6-difluorophenyl)-5-ethoxy-8-fluoro-1,2,4-triazolo[1,5-c]pyrimidine-2-sulfamide N-benzoyl-N-(2,6-difluorophenyl)-5-ethoxy-8-fluoro-1,2,4-triazolo[1,5-c]pyrimidine-2-sulfamide is prepared by a method similar to that in embodiment 1, and the HPLC purity is 98.5%. $^1$H NMR (400 MHz, D6-DMSO) δ: 8.40 (d, 1H), 7.56-7.59 (m, 1H), 7.51 (t, 2H), 7.42 (d, 1H), 7.37 (t, 2H), 7.28 (t, 2H), 4.27 (s, 3H).

Embodiment 23 Preparation of N-acetyl-N-(2,6-difluorophenyl)-5-methyl-1,2,4-triazolo[1,5-a]pyrimidine-2-sulfamide The N-acetyl-N-(2,6-difluorophenyl)-5-methyl-1,2,4-triazolo[1,5-a]pyrimidine-2-sulfamide is prepared by a method similar to that in embodiment 1, and the HPLC purity is 97.9%. $^1$H NMR (400 MHz, D6-DMSO) δ: 9.45 (d, 1H), 7.66 (d, 1H), 7.55 (d, 1H), 7.36 (t, 2H), 7.36 (t, 2H), 2.71 (s, 3H), 2.38 (s, 3H).

Embodiment 24 Preparation of N-(2-chloracetyl)-N-(2,6-difluorophenyl)-5-methyl-1,2,4-triazolo[1,5-a]pyrimidine-2-sulfamide N-(2-chloracetyl)-N-(2,6-difluorophenyl)-5-methyl-1,2,4-triazolo[1,5-a]pyrimidine-2-sulfamide is prepared by a method similar to that in embodiment 1, and the HPLC purity is 99.2%. $^1$H NMR (400 MHz, D6-DMSO) δ: 9.46 (d, 1H), 7.70-7.73 (m, 1H), 7.57 (d, 1H), 7.38 (t, 2H), 4.27 (s, 2H), 2.69 (s, 3H).

Embodiment 25 Preparation of N-(2,2-dichloroacetyl)-N-(2,6-difluorophenyl)-5-methyl-1,2,4-triazolo[1,5-a]pyrimidine-2-sulfamide N-(2,2-dichloroacetyl)-N-(2,6-difluorophenyl)-5-methyl-1,2,4-triazolo[1,5-a]pyrimidine-2-sulfamide is prepared by a method similar to that in embodiment 1, and the HPLC purity is 97.2%. $^1$H NMR (400 MHz, D6-DMSO) δ: 9.45 (d, 1H), 7.71 (d, 1H), 7.55 (d, 1H), 7.36 (t, 2H), 7.17 (s, 1H), 2.69 (s, 3H).

Embodiment 26 Preparation of N-(2-methoxyacetyl)-N-(2,6-difluorophenyl)-5-methyl-1,2,4-triazolo[1,5-a]pyrimidine-2-sulfamide N-(2-methoxyacetyl)-N-(2,6-difluorophenyl)-5-methyl-1,2,4-triazolo[1,5-a]pyrimidine-2-sulfamide is prepared by a method similar to that in embodiment 1, and the HPLC purity is 98.8%. $^1$H NMR (400 MHz, D6-DMSO) δ: 9.45 (d, 1H), 7.68-7.70 (m, 1H), 7.55 (d, 1H), 7.36 (t, 2H), 4.50 (s, 2H), 3.28 (s, 3H), 2.71 (s, 3H).

Embodiment 27 Preparation of N-acetyl-N-(2,6-difluorophenyl)-5-ethoxy-8-fluoro-1,2,4-triazolo[1,5-c]pyrimidine-2-sulfamide N-acetyl-N-(2,6-difluorophenyl)-5-ethoxy-8-fluoro-1,2,4-triazolo[1,5-c]pyrimidine-2-sulfamide is prepared by a method similar to that in embodiment 1, and the HPLC purity is 99.3%. $^1$H NMR (400 MHz, D6-DMSO) δ: 8.41 (d, 1H), 7.69-7.72 (m, 1H), 7.41 (t, 2H), 4.25 (s, 3H), 2.33 (s, 3H).

Embodiment 28 Preparation of N-t-butyloxycarboryl-N-(2,6-difluorophenyl)-5-ethoxy-7-fluoro-1,2,4-triazolo[1,5-c]pyrimidine-2-sulfamide N-t-butyloxycarboryl-N-(2,6-difluorophenyl)-5-ethoxy-7-fluoro-1,2,4-triazolo[1,5-c]pyrimidine-2-sulfamide is prepared by a method similar to that in embodiment 1, and the HPLC purity is 96.8%. $^1$H NMR (400 MHz, D6-DMSO) δ: 1.43 (t, 3H), 1.67 (s, 9H), 4.78 (q, 2H), 6.82 (s, 1H), 7.22 (t, 1H), 7.35 (d, 2H).

Embodiment 29 Preparation of N-(2,6-dichlorophenyl)-5-ethoxy-7-fluoro-1,2,4-triazolo[1,5-c]pyrimidine-2-sulfamide The preparation method comprises the following steps:
adding the N-t-butyloxycarboryl-N-(2,6-difluorophenyl)-5-ethoxy-7-fluoro-1,2,4-triazolo[1,5-c]pyrimidine-2-sulfamide (5.06 g, 1.0 eq) prepared in embodiment 28, 1 mL of concentrated hydrochloric acid and ethanol (50 mL) into a 250 mL reaction flask equipped with a mechanical stirrer, raising the temperature to 60° C. and continuously stirring and reacting for about 2 h, cooling the reaction solution to room temperature when the raw materials are completely reacted as determined by HPLC, filtering, washing a filter cake with little ethanol, and drying to a constant weight to obtain 3.97 g white solid with HPLC purity of 99.9%. $^1$H NMR (400 MHz, D6-DMSO) δ: 11.05 (s, 1H), 7.51 (m, 2H), 7.37 (m, 2H), 4.65 (m, 2H), 1.47 (m, 3H).

Embodiment 30 Preparation of N-(2,6-dichlorophenyl)-5-ethoxy-7-fluoro-1,2,4-triazolo[1,5-c]pyrimidine-2-sulfamide The preparation method comprises the following steps:
adding the N-acetyl-N-(2,6-dichlorophenyl)-5-ethoxy-7-fluoro-1,2,4-triazolo[1,5-c]pyrimidine-2-sulfamide (10.3 g, 1.0 eq) prepared in embodiment 1, anhydrous sodium carbonate (2.4 g, 1.0 eq) and absolute methanol (100 mL) into a 250 mL reaction flask equipped with a mechanical stirrer, raising the temperature to 55° C. and continuously stirring and reacting for about 5 h, cooling a reaction solution to room temperature when the raw materials are completely reacted as determined by HPLC, filtering, washing a filter cake with cold water, and drying to a constant weight to obtain 8.3 g white solid with HPLC purity of 99.9%. $^1$H NMR (400 MHz, D6-DMSO) δ: 11.05 (s, 1H), 7.51 (m, 2H), 7.37 (m, 2H), 4.65 (m, 2H), 1.47 (m, 3H).

Embodiment 31 Preparation of N-(2,6-dichlorophenyl)-5-ethoxy-7-fluoro-1,2,4-triazolo[1,5-c]pyrimidine-2-sulfamide The preparation method comprises the following steps:
adding the N-(2-bromoacetyl)-N-(2,6-dichlorophenyl)-5-ethoxy-7-fluoro-1,2,4-triazolo[1,5-c]pyrimidine-2-sulfamide (12.3 g, 1.0 eq) prepared in embodiment 2, sodium bicarbonate (2.0 g, 1.0 eq) and absolute isopropanol (100 mL) into a 250 mL reaction flask equipped with a mechanical stirrer, raising the temperature to 60° C. and continuously stirring and reacting for about 6 h, cooling a reaction solution to room temperature when the raw materials are completely reacted as determined by HPLC, filtering, washing the filter cake with cold water, filtering, and drying to a constant weight to obtain 8.0 g white solid with HPLC purity of 99.9%. $^1$H NMR (400 MHz, D6-DMSO) δ: 11.05 (s, 1H), 7.51 (m, 2H), 7.37 (m, 2H), 4.65 (m, 2H), 1.47 (m, 3H).

Embodiment 32 Preparation of N-(2,6-dichlorophenyl)-5-ethoxy-7-fluoro-1,2,4-triazolo[1,5-c]pyrimidine-2-sulfamide The preparation method comprises the following steps:
adding the N-(2-chloracetyl)-N-(2,6-dichlorophenyl)-5-ethoxy-7-fluoro-1,2,4-triazolo[1,5-c]pyrimidine-2-sulfamide (11.4 g, 1.0 eq) prepared in embodiment 3, potassium carbonate (3.2 g, 1.0 eq) and absolute ethyl alcohol (100 mL) into a 250 mL reaction flask equipped with a mechanical stirrer, raising the temperature to 60° C. and continuously stirring and reacting for about 6 h, cooling a reaction solution to room temperature when the raw materials are completely reacted as determined by HPLC, filtering, washing the filter cake with cold water, filtering, and drying to a constant weight to obtain 8.4 g white solid with HPLC purity of 99.9%. $^1$H NMR (400 MHz, D6-DMSO) δ: 11.05 (s, 1H), 7.51 (m, 2H), 7.37 (m, 2H), 4.65 (m, 2H), 1.47 (m, 3H).

Embodiment 33 Preparation of N-(2,6-dichlorophenyl)-5-ethoxy-7-fluoro-1,2,4-triazolo[1,5-c]pyrimidine-2-sulfamide The preparation method comprises the following steps:
adding the N-(2,2-dichloroacetyl)-N-(2,6-dichlorophenyl)-5-ethoxy-7-fluoro-1,2,4-triazolo[1,5-c]pyrimidine-2-sulfamide (11.6 g, 1.0 eq) prepared in embodiment 4, potassium carbonate (2.0 g, 1.0 eq) and absolute ethyl alcohol (100 mL) into a 250 mL reaction flask equipped with a mechanical stirrer, raising the temperature to 60° C. and continuously stirring and reacting for about 6 h, cooling a reaction solution to room temperature when the raw materials are completely reacted as determined by HPLC, filtering, washing the filter cake with cold water, filtering, and drying to a constant weight to obtain 7.9 g white solid with HPLC purity of 99.9%. $^1$H NMR (400 MHz, D6-DMSO) δ: 11.05 (s, 1H), 7.51 (m, 2H), 7.37 (m, 2H), 4.65 (m, 2H), 1.47 (m, 3H).

What is claimed is:
1. A method for preparing a high-purity sulfonamide compound, comprising:
a, reacting with a compound of a formula (II) under the action of a solvent, a base and a catalyst by taking a crude sulfonamide compound (I) as an initial raw material, so as to synthesize a compound of a formula (III); and
b, enabling the compound represented by the formula (III) to react with a base or an acid in a solvent and obtaining the sulfonamide compound (I) having a purity of 99% or higher;
a general formula of the reactions is as follows:

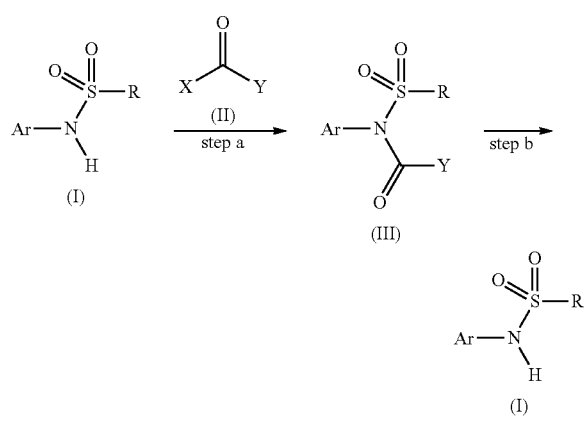

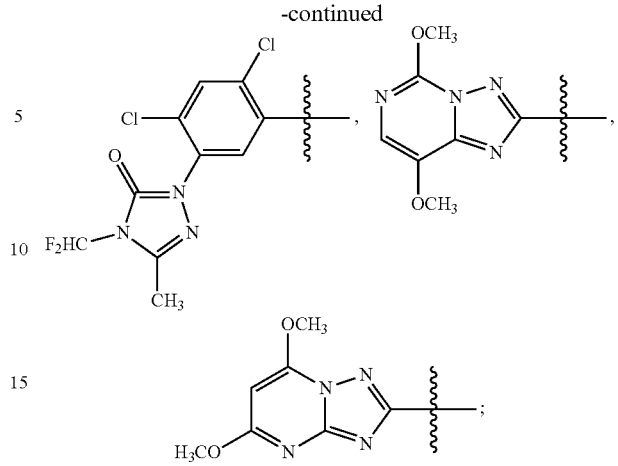

wherein R is methyl, or aryl or heteroaryl shown as follows:

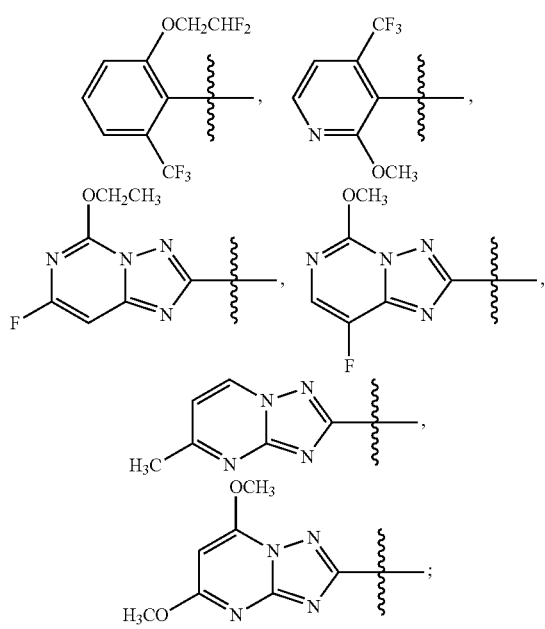

Ar is aryl or heteroaryl shown as follows:

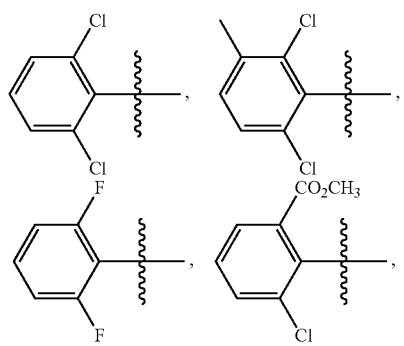

X is halogen or test-butoxy carbonyloxy; and
Y is C1-C6 alkyl, C6-C12 aryl or tert-butoxy.

2. The method according to claim 1, wherein X is Cl or tert-butoxy carbonyloxy, and C1-C6 alkyl or tert-butoxy.

3. The method according to claim 1, wherein a molar ratio of the compound (II) to the crude product of the sulfonamide compound (I) is (0.8-2):1.

4. The method according to claim 1, wherein the base in the step a is an organic base; a molar ratio of the organic base to the crude sulfonamide compound (I) is (1-2):1; the catalyst is 4-dimethylaminopyridine; a weight percentage of the catalyst to the crude sulfonamide compound (I) is 0.05-10%; the solvent is selected from the group consisting of halohydrocarbons, ether, and nitriles; and a reaction temperature is −10° C.-80° C.

5. The method according to claim 4, wherein the organic base in the step a is triethylamine, DBU or pyridine; the is solar ratio of the organic base to the crude product of the sulfonamide compound (I) is (1-1.3):1; the weight percentage of the catalyst to the crude product of the sulfonamide compound (I) is 0.1-5%; the solvent is dichloromethane, tetrahydrofuran, or acetonitrile; and the reaction temperature is 0° C.-40° C.

6. The method according to claim 1, wherein the base in the step b is a hydroxide, carbonate or hydrocarbonate of alkali metals and alkaline-earth metals, a molar ratio of the base to the compound (III) is (0.5-1.5):1, the solvent is methanol, ethanol, isopropanol, acetonitrile, acetone, DMF or DMSO, and a reaction temperature is 0° C.-80° C.; or the acid in the step b refers to an inorganic acid or an organic acid, a molar ratio of the acid to the compound (III) is (0.5-1.5):1, the solvent refers to methanol, ethanol, isopropanol, acetonitrile, acetone, DMF or DMSO, and a reaction temperature is 0° C.-80° C.

7. The method according to claim 6, wherein the base in the step b is sodium carbonate, potassium carbonate, sodium bicarbonate or potassium bicarbonate, the molar ratio of the base to the compound (III) is (0.75-1.25):1, the solvent is ethanol, and the reaction temperature is 10° C.-60° C.; or the acid in the step b is hydrochloric acid, sulfuric acid or trifluoroacetic acid, the molar ratio of the acid to the compound (III) is (0.75-1.25):1, the solvent is ethanol, and the reaction temperature is 10° C.-60° C.

* * * * *